(12) United States Patent
Kim

(10) Patent No.: US 7,569,677 B2
(45) Date of Patent: *Aug. 4, 2009

(54) ANTIBIOTIC-CONJUGATED ANTIBODIES

(75) Inventor: Stanley A. Kim, Wellington, FL (US)

(73) Assignee: STROX Biopharmaceuticals, LLC, Wellington, FL (US)

( * ) Notice: Subject to any disclaimer, the term of this patent is extended or adjusted under 35 U.S.C. 154(b) by 1403 days.

This patent is subject to a terminal disclaimer.

(21) Appl. No.: 10/184,222

(22) Filed: Jun. 27, 2002

(65) Prior Publication Data

US 2002/0168368 A1    Nov. 14, 2002

Related U.S. Application Data

(60) Continuation of application No. 09/965,763, filed on Sep. 27, 2001, now Pat. No. 6,475,788, which is a division of application No. 09/378,147, filed on Aug. 20, 1999, now Pat. No. 6,322,788.

(60) Provisional application No. 60/097,291, filed on Aug. 20, 1998.

(51) Int. Cl.
*C07K 16/00*     (2006.01)

(52) U.S. Cl. .............. 530/389.1; 530/389.5; 530/391.1; 530/391.3; 530/391.7

(58) Field of Classification Search ....................... None
See application file for complete search history.

(56) References Cited

U.S. PATENT DOCUMENTS

| | | | | |
|---|---|---|---|---|
| 4,867,973 A | * | 9/1989 | Goers et al. ............. | 424/181.1 |
| 5,258,499 A | * | 11/1993 | Konigsberg et al. ......... | 530/351 |
| 5,545,721 A | * | 8/1996 | Carroll et al. ............ | 530/391.7 |

OTHER PUBLICATIONS

Kohno et al, Drug delivery systems for infection: Liposome-incorporating antimicrobial drugs, 1998, J Infect Chemother, vol. 4, p. 159-73.*

* cited by examiner

*Primary Examiner*—Mark Navarro
(74) *Attorney, Agent, or Firm*—Stanley A Kim

(57) ABSTRACT

A composition including a purified antibody conjugated with at least one antibiotic, the antibody having an antigen-binding portion that binds at least one antigen derived from Staphylococcus or Streptococcus.

10 Claims, No Drawings

ANTIBIOTIC-CONJUGATED ANTIBODIES

CROSS-REFERENCE TO RELATED APPLICATIONS

The present application is a continuation of U.S. patent application Ser. No. 09/965,763 now U.S. Pat. No. 6,475,788 which was filed on Sep. 27, 2001 as a divisional of U.S. patent application Ser. No. 09/378,147 (now U.S. Pat. No. 6,322,788) which was filed on Aug. 20, 1999 and claimed the priority of U.S. provisional patent application No. 60/097,291 filed Aug. 20, 1998.

BACKGROUND OF THE INVENTION

The invention relates to the field of antibodies, immunology, infectious diseases, and medicine.

Pathogenic bacteria are a substantial cause of sickness and death in both humans and animals. Prominent among these is *Staphylococcus aureus* (*S. aureus*). Infection with these gram-positive cocci often results in the development of a superficial abscess. Other cases of *S. aureus* infection are more serious. For example, intrusion of *S. aureus* into the lymphatics and blood, can lead to a systemic infection which, in turn, can cause complications such as endocarditis, arthritis, osteomyelitis, pneumonia, septic shock and even death.

Streptococci also cause a large number of infections in humans and animals. Although many infections with streptococci are mild in nature, others can result in profound illness. Diseases associated with streptococcal infection include superficial cutaneous infections, pharyngitis, tonsilitis, impetigo, erysipelas, scarlet fever, urinary tract infections, endocarditis, acute rheumatic fever, acute glomerulonephritis, necrotizing fasciitis, and bacteremia. Severe cases of streptococcal infection can also lead to septic shock and death.

For most of this century, standard treatment for bacterial infections has been antibiotic therapy. Unfortunately, over the last several decades, several pathogenic strains of bacteria have developed resistance to various antibiotics. Worse, some of these strains have acquired resistance to multiple antibiotics. The advent of methicillin-resistant *S. aureus* in the last decade is perhaps the most significant example of this phenomenon. Vancomycin has thus become the antibiotic of choice for treating methicillin-resistant *S. aureus* infections. Recently, *S. aureus* strains displaying intermediate resistance to vancomycin have emerged. MMWR, 46:813-815, 1997.

SUMMARY OF THE INVENTION

The invention relates to antibodies that are capable of binding to a bacterial antigen, but lack the ability to be bound by bacterial Fc-binding proteins (e.g., staphylococcal Protein A, streptococcal Protein G, streptococcal protein H, etc.). Preparations of such antibodies should be effective for treating infections caused by bacteria that express Fc-binding proteins.

Effective antibody-mediated clearance of a bacterial infection generally requires the participation of two portions of an antibody molecule. The antigen-binding portion (e.g., the variable region of the Fab portion) of an antibody molecule serves to direct the antibody to a bacterial cell by physically engaging an antigen on that bacterial cell surface. The effector portion (e.g., the constant region or Fc region) of an antibody bound on the bacterial cell surface attracts effector molecules (e.g., complement or Fc receptors) that directly or indirectly kill the bacterium. Thus, an antibody bound to a bacterium typically has its antigen-binding portion directed toward the bacterial surface and its effector portion directed away from the bacterial cell surface. This orientation is thought to allow the effector portion of an antibody to physically interact with effector molecules and thereby facilitate the immune system-mediated clearance of bacteria. In bacteria expressing bacterial Fc-binding proteins, however, bacteria-specific antibodies may be bound to the bacterial cell surface in an opposite orientation (i.e., with the effector portion directed towards the bacterial cell surface and the antigen-binding portion directed away from the bacterial cell surface). In the latter orientation, the effector portion of an antibody is sterically obscured by the bacterial Fc-binding protein and thus not readily able to bind effector molecules. In this manner, bacterial Fc-binding proteins may help the bacteria evade clearance by the immune system.

Accordingly, the present invention features a composition containing a purified polyclonal antibody enriched for immunoglobulins having both an antigen-binding portion specific for a bacterial antigen (e.g., a *S. aureus* antigen) and a constant region that does not bind a bacterial Fc-binding protein. The invention also features a composition containing a purified monoclonal antibody having both an antigen-binding portion specific for a bacterial antigen and a constant region that does not bind a bacterial Fc-binding protein. In addition, the invention includes a composition containing a polyclonal antibody that is made up primarily of a mixture of two or more monoclonal antibodies, each of which has both an antigen-binding portion specific for a bacterial antigen and a constant region that does not bind a bacterial Fc-binding protein.

In one aspect of the invention, the antibodies featured in the above compositions are derived from an animal possessing immunoglobulins, such as a mammal (e.g., a rat, mouse, rabbit, guinea pig, hamster, cow, pig, sheep, goat, horse, dog, or cat). In another aspect of the invention, the antibodies are derived from a human.

Also within the invention are compositions including an antibody that has both an antigen-binding portion directed against gram-positive bacteria and a constant region that does not bind a bacterial Fc-binding protein. In one embodiment, the compositions of the invention include an antibody having both an antigen-binding portion specific for Staphylococcus strains expressing Protein A (e.g., *S. aureus*) and a constant region that does not bind a bacterial Fc-binding protein. In another embodiment, the compositions include an antibody having both an antigen-binding portion specific for Streptococcus strains expressing Protein G (e.g., group C streptococci) and a constant region that does not bind a bacterial Fc-binding protein.

In one facet of the invention, the anti-bacterial antibodies featured in the above compositions have constant regions that do not bind to a particular Fc-binding protein. In one example, the featured antibody has a constant region that does not bind Protein A. In another example, the featured antibody has a constant region that does not bind Protein G.

In various embodiments, the antibodies within the invention are unmodified (i.e., not conjugated to an exogenous molecule). In other embodiments, the antibodies within the invention are conjugated to an antibiotic.

The invention additionally features pharmaceutical compositions that include one of the foregoing antibody compositions and a pharmaceutically acceptable carrier. Thus, for example, the invention includes a composition having a purified polyclonal antibody enriched for immunoglobulins having both an antigen-binding portion specific for a bacterial antigen and a constant region that does not bind a bacterial Fc-binding protein, and a pharmaceutically acceptable carrier. Likewise, the invention features a composition including a purified monoclonal antibody having both an antigen-binding portion specific for a bacterial antigen and a constant region that does not bind a bacterial Fc-binding protein, and a pharmaceutically acceptable carrier.

Also within the invention are processes of preparing pharmaceutical compositions. One such process includes the steps of: obtaining isolated immunoglobulins from an animal; contacting the isolated immunoglobulins with a bacterial Fc-binding protein; collecting the immunoglobulins not bound to the bacterial Fc-binding protein; and adding a pharmaceutically acceptable carrier to the immunoglobulins not bound to the bacterial Fc-binding protein. Another process within the invention includes the steps of: immunizing an animal with at least one bacterial antigen; isolating immunoglobulins from the animal; contacting the isolated immunoglobulins with a bacterial Fc-binding protein; collecting the immunoglobulins not bound to the bacterial Fc-binding protein; and adding a pharmaceutically acceptable carrier to the immunoglobulins not bound to the bacterial Fc-binding protein. In one embodiment of the latter process, the bacterial antigen used to immunize the animal is derived from *Staphylococcus aureus*. In another embodiment of the latter process, the bacterial antigen is derived from Streptococcus. In embodiments of each of the foregoing processes, the Fc-binding protein used is Protein A. And in other embodiments of each of the foregoing processes, the Fc-binding protein used is Protein G.

The invention also features a method of treating an animal or human having a *Staphylococcus aureus* infection. One embodiment of this method includes the step of: administering to an animal or human a therapeutically effective amount of a composition containing a purified polyclonal antibody enriched for immunoglobulins having both an antigen-binding portion specific for a *S. aureus* antigen and a constant region that does not bind a bacterial Fc-binding protein. Another embodiment of this method includes the step of: administering to an animal or human a therapeutically effective amount of a composition containing a purified monoclonal antibody that has both an antigen-binding portion specific for a *S. aureus* antigen and a constant region that does not bind a bacterial Fc-binding protein.

The invention also features a method of preventing a *Staphylococcus aureus* infection in an animal or a human. One embodiment of this method includes the step of: administering to an animal or human a therapeutically effective amount of a composition containing a purified polyclonal antibody enriched for immunoglobulins having both an antigen-binding portion specific for a *S. aureus* antigen and a constant region that does not bind a bacterial Fc-binding protein. Another embodiment of this method includes the step of: administering to an animal or human a therapeutically effective amount of a composition containing a purified monoclonal antibody that has both an antigen-binding portion specific for a *S. aureus* antigen and a constant region that does not bind a bacterial Fc-binding protein.

In addition, the invention features a method of treating an animal or human having a streptococcal infection. One embodiment of this method includes the step of: administering to an animal or human a therapeutically effective amount of a composition containing a purified polyclonal antibody enriched for immunoglobulins having both an antigen-binding portion specific for a streptococcal antigen and a constant region that does not bind a bacterial Fc-binding protein. Another embodiment of this method includes the step of: administering to an animal or human a therapeutically effective amount of a composition containing a purified monoclonal antibody that has both an antigen-binding portion specific for a streptococcal antigen and a constant region that does not bind a bacterial Fc-binding protein.

The invention also features a method of preventing a streptococcal infection in an animal or a human. One embodiment of this method includes the step of: administering to an animal or human a therapeutically effective amount of a composition containing a purified polyclonal antibody enriched for immunoglobulins having both an antigen-binding portion specific for a streptococcal antigen and a constant region that does not bind a bacterial Fc-binding protein. Another embodiment of this method includes the step of: administering to an animal or human a therapeutically effective amount of a composition containing a purified monoclonal antibody that has both an antigen-binding portion specific for a streptococcal antigen and a constant region that does not bind a bacterial Fc-binding protein.

As used herein, an "antibody" is an immunoglobulin, a solution of identical or heterogeneous immunoglobulins, or a mixture of immunoglobulins.

A "monoclonal antibody" is an antibody expressed by one clonal B cell line. As used herein, the term refers to a population of antibody molecules that contains only one species of an antigen binding site capable of immunoreacting with a particular epitope of a particular antigen.

A "polyclonal antibody" is a mixture of heterogeneous antibodies. Typically, a polyclonal antibody will include myriad different antibodies molecules which bind a particular antigen or particular organism with at least some of the different antibodies immunoreacting with a different epitope of the antigen or organism. As used herein, a polyclonal antibody can be a mixture of two or more monoclonal antibodies.

An "antigen-binding portion" of an antibody is contained within the variable region of the Fab portion of an antibody and is the portion of the antibody that confers antigen specificity to the antibody (i.e., typically the three-dimensional pocket formed by the complementarity-determining regions of the heavy and light chains of the antibody). An "Fab portion" or "Fab region" is the proteolytic fragment of a papain-digested immunoglobulin that contains the antigen-binding portion of that immunoglobulin. A "non-Fab portion" is that portion of an antibody not within the Fab portion, e.g., an Fc portion.

A "constant region" of an antibody is that portion of the antibody outside of the variable region. Generally encompassed within the constant region is the "effector portion" of an antibody, which is the portion of an antibody that is responsible for binding other immune system components that facilitate the immune response. Thus, for example, the site on an antibody that binds complement components or Fc receptors (not via its antigen-binding portion) is an effector portion of that antibody. Also included within the constant region is the "Fc region" or "Fc portion", which is the proteolytic fragment of a papain-digested immunoglobulin that does not contain the antigen-binding portion of that immunoglobulin A "bacterial Fc-binding protein" is a polypeptide-based molecule derived from a bacterial microorganism (e.g., purified from bacteria, produced by recombinant DNA technology, or synthesized chemically from a known amino acid sequence) that specifically binds the Fc portion (and in some cases the constant region of the Fab portion) of at least one type of immunoglobulin. Common examples of bacterial Fc-binding proteins include Protein A and Protein G. As used herein, the terms "Protein A" and "Protein G" include both native forms of the proteins and mutant forms of the proteins (whether naturally-occurring or man-made) that retain the ability to bind to the constant region of at least one type of immunoglobulin.

By the term "protein" is meant any chain of amino acids and includes peptides, polypeptides, proteins, and modified proteins such as glycoproteins, lipoproteins, phosphoproteins, metalloproteins, and the like.

When referring to a protein molecule such as an antibody, "purified" means separated from components that naturally accompany such molecules. Typically, an antibody or protein is purified when it is at least 30% (e.g., 40%, 50%, 60%, 70%, 80%, 90%, and 100%), by weight, free from the proteins or other naturally-occurring organic molecules with which it is naturally associated. Purity can be measured by any appropriate method, e.g., column chromatography, polyacrylamide gel electrophoresis, or HPLC analysis. A chemically-synthesized protein or other recombinant protein produced in a cell type other than the cell type in which it naturally occurs is "purified." An antibody containing a desired immunoglobulin type and an undesired immunoglobulin type is "enriched" for the desired immunoglobulin type when treatment of the antibody results in a higher ratio of desired immunoglobulin to undesired immunoglobulin after treatment then before treatment. For example, a solution of antibody containing Protein A-binding immunoglobulins and non-Protein A-binding immunoglobulins is enriched for the latter when some of all of the Protein A-binding antibodies are removed from the solution.

By "bind", "binds", or "reacts with" is meant that one molecule recognizes and adheres to a particular second molecule in a sample, but does not substantially recognize or adhere to other molecules in the sample (e.g., Protein A "binds" to the constant region of Human IgGI but not to Chicken IgG). Generally, an antibody that "specifically binds" another molecule has a binding affinity greater than about $10^5$ to $10^6$ liters/mole for that other molecule.

A "therapeutically effective amount" is an amount which is capable of producing a medically desirable effect in a treated animal or human (e.g., amelioration or prevention of a disease).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the materials, methods, and examples are illustrative only and not intended to be limiting.

Other features and advantages of the invention will be apparent from the following detailed description, and from the claims.

DETAILED DESCRIPTION

The present invention relates to anti-bacterial antibodies that do not react with bacterial Fc-binding proteins. These antibodies bind bacteria expressing Fc-binding proteins via the antigen-binding portion of their Fab regions, leaving the effector portion-containing constant regions of these antibodies oriented away from the bacterial cell surface and free to engage other molecules. Thus, the effector functions of these antibodies should be fully functional (i.e., able to effect complement fixation, opsinization, etc.). In comparison to the above antibodies, antibacterial antibodies that react with bacterial Fc-binding proteins may bind bacteria expressing Fc-binding proteins via their constant regions. In this case, the effector portions of these antibodies would be sterically-obscured by the bacterial Fc-binding proteins and hence partially or wholly unavailable for binding effector molecules such as complement components or Fc receptors on phagocytes.

Although the above immunoglobulins lack a constant region capable of binding bacterial Fc-binding proteins, this does not limit the featured antibodies to those lacking a constant region. On the contrary, in order to be effective against bacteria, the immunoglobulins of the invention should generally have an effector region capable of mediating an immune response (e.g., complement fixation or opsinization). Thus, typically, the immunoglobulins of the invention have an intact constant region. For example, human immunoglobulins such as $IgG_3$ (allotype with arginine at amino acid position 435) possess an intact constant region yet lack reactivity for Protein A or Protein G. Immunoglobulins with a truncated or mutated constant regions (e.g., the portion of constant region that binds a bacterial Fc-binding protein is ablated) are also within the invention if they are capable of mediating an immune response. Also within the invention are immunoglobulins that have an antigen-binding portion specific for a bacterial antigen, but lack both a constant region that reacts with a bacterial Fc-binding protein and an effector region capable of mediating an immune response. These immunoglobulins are conjugated with an antibiotic (e.g., antibiotic-conjugated anti-staphylococcal Fab fragments). The antigen-binding portion of these immunoglobulins permits them to bind to and deliver the antibiotic to a bacterium. Hence, rather than relying on immune system effectors (e.g., complement or Fc receptors), these immunoglobulins are directly bactericidal or bacteriostatic.

Animals usually respond to a bacterial infection by producing antibodies against the bacteria. These antibodies help clear the infection by two general methods. In complement-mediated lysis, components of the complement system (e.g., Clq) bind to the constant region of antibodies attached to the cell wall of the bacteria. This interaction triggers various enzymatic events (e.g., the classical pathway and the alternative pathway) which cause the formation of a membrane attack complex that bores holes through bacterial membranes. These holes disrupt the integrity of the bacterial membrane and thus can result in bacterial death. In opsinization, the constant regions of antibodies coating a bacterium directly or indirectly interact with receptors (e.g., Fc receptors or complement receptors) on a phagocyte (e.g., a macrophage, monocyte, or neutrophil). By increasing the affinity of a phagocyte for a bacterium and/or activating the phagocyte, this interaction facilitates the bacterium being phagocytosed and destroyed by the phagocyte. Unfortunately, complement-mediated lysis and opsinization may not function efficiently when the pathogenic bacteria express Fc-binding proteins. This is likely so because the bacterial Fc-binding protein competes with effector molecules (e.g., complement and Fc receptors) for binding to the constant region of the antibacterial antibodies.

Common bacterial Fc-binding proteins include: staphylococcal Protein A and streptococcal Protein G. Protein A is a polypeptide isolated from some strains of *S. aureus*. Protein G is a polypeptide isolated from some strains of group C streptococci. Both Protein A and Protein G bind the constant region of many immunoglobulin molecules without interacting with the antigen binding site. Surolia et al., *Trends Biochem. Sci.*, 7:74 (1981); Bjorck et al., *J. Immunol.*, 133:969 (1984).

Materials and Methods

Antibodies

Antibacterial antibodies can be produced by any one of several methods known in the art. E.g., Yoshida et al., *Experientia* 43:329, 1987; Yoshida and Ichiman, *J. Clin. Microbiol* 20:461, 1984; and U.S. Pat. No. 5,770,208. Classically, antigen-specific antibodies are produced by immunizing a host animal with the antigen, and later collecting the antibody-containing serum from the animal. For raising bacteria-specific antibodies, the antigen typically used is live, attenuated, fixed or killed whole bacteria ("whole bacterial antigen"). For raising antibodies specific for one or more particular bacterial antigens, one or more protein antigens, peptide fragments thereof, or polysaccharide antigens derived from the bacteria ("purified antigens") are used to immunize host animals. Purified antigens can be a homogenous preparation of one antigen derived from one or more bacterial strains or a combination of several different antigens isolated from one or more bacterial strains. To enhance the immune response, antigens (especially small peptide antigens) may be made more immunogenic by coupling to a carrier protein, such as keyhole limpet hemocyanin (KLH). See, e.g., Ausebel et al., *Current Protocols in Molecular Biology*, John Wiley & Sons, Inc., NY, 1989.

Antibacterial antibodies may also be purchased commercially. For example, anti-*S. aureus* antibodies may be purchased from Chemicon (Temecula, Calif.) and anti-streptococcal antibodies may be purchased from Cortex Biochem (San Leandro, Calif.). Alternatively, pooled immunoglobulin may be used. Pooled immunoglobulin may be obtained by combining immunoglobulins isolated from several hosts. Pooled immunoglobulin can also obtained from commercial suppliers. E.g., Gamimmune®, Bayer Biological, West Haven, Conn.; Sandoglobulin®, Novartis Pharmaceuticals Corporation, East Hanover, N.J. Lots of pooled immunoglobulin can be checked for reactivity against a particular bacterial species using techniques well known in the art. See, e.g., Garvey et al., *Methods in Immunology*, W.A. Benjamin, Inc., Reading, Mass., 1977. Those lots having reactivity for the bacterial antigen of interest can be used in the invention. For example, lots of pooled normal human immunoglobulin are examined for antibodies that specifically bind *S. aureus* antigens using immunoprecipitation assays. In the latter example, if necessary, Fc-binding to Protein A can be excluded from consideration by using F(ab')2 fragments of the immunoglobulin or by first adsorbing out Protein A-binding activity from the immunoglobulin.

Any animal capable of producing antibodies in response to an antigen may be used in the invention. Commonly used animals include: mice, rats, horses, cows, goats, sheep, rabbits, cats, dogs, guinea pigs, chickens and humans. Host animals are immunized by injection with purified or whole bacterial antigen. Preferably, after the first immunization, the host animal receives one or more booster injections of antigen to augment antibody production and affinity. For immunization of humans, care should be taken to select the appropriate antigen, adjuvant, and/or carrier protein to avoid potential adverse reactions (e.g., granuloma formation with Freund's complete adjuvant; anaphylactic shock).

To enhance the immunologic response, antigens, whether purified or whole bacterial, are typically mixed with adjuvant before injection into a host animal or human. Adjuvants useful in augmenting antibody production include Freund's adjuvant (complete and incomplete), mineral gels such as aluminum hydroxide, surface active substances such as lysolecithin, pluronic polyols, polyanions, peptides, oil emulsions, KLH, and dinitrophenol (DNP). Examples of potentially useful human adjuvants include BCG (bacille Calmette-Guerin) and *Corynebacterium parvum*.

Antigens can also be cross-linked or incorporated into lipid vesicles to enhance their antigenicity.

Antibodies within the invention include without limitation polyclonal antibodies, monoclonal antibodies, humanized, and chimeric antibodies. Polyclonal antibodies can be isolated by collecting sera from immunized host animals. Monoclonal antibodies can be prepared using the whole bacterial, protein, peptide, or polysaccharide antigens discussed above and standard hybridoma technology. See, e.g., Kohler et al., *Nature,* 256:495, 1975; Kohler et al., *Eur. J. Immunol.* 6:511, 1976; Kohler et al., *Eur. J. Immunol.* 6:292, 1976; Hammerling et al., "Monoclonal Antibodies and T cell Hybridomas," Elsevier, N.Y., 1981; Coligan et al., *Current Protocols in Immunology*, John Wiley & Sons, NY, 1997. Human monoclonal antibodies are prepared by immortalizing a human antibody secreting cell (e.g., a human plasma cell). See, e.g., U.S. Pat. No. 4,634,664. To obtain monoclonal antibodies, hybridomas or other immortalized antibody secreting cells are cultivated in vitro (e.g., in tissue culture) or in vivo (e.g., in athymic or SCID mice). Antibodies are isolated by collecting the in vitro culture medium or bodily fluids (e.g., serum or ascites) from the in vivo cultures.

Additionally, chimeric antibodies, which are antigen-binding molecules having different portions derived from different animal species (e.g., variable region of a rat immunoglobulin fused to the constant region of a human immunoglobulin), are expected to be useful in the invention. Such chimeric antibodies can be prepared by methods known in the art. E.g., Morrison et al., *Proc. Nat'l. Acad. Sci. USA,* 81:6851, 1984; Neuberger et al., *Nature,* 312:604, 1984; Takeda et al., *Nature,* 314:452, 1984. Similarly, antibodies can be humanized by methods known in the art. For example, monoclonal antibodies with a desired binding specificity can be commercially humanized (Scotgene, Scotland; Oxford Molecular, Palo Alto, Calif.) or as described in U.S. Pat. Nos. 5,693,762; 5,530,101; or 5,585,089. In a like manner, portions of the constant region of Protein A- or Protein G-binding immunoglobulins can be altered, deleted or mutated to remove Protein A or Protein G reactivity.

Once isolated, antibodies can be further purified by conventional techniques including: salt cuts (e.g., saturated ammonium sulfate precipitation), cold alcohol fractionation (e.g., the Cohn-Oncley cold alcohol fractionation process), size exclusion chromatography, ion exchange chromatography, immunoaffinity chromatography (e.g., chromatography beads coupled to antihuman immunoglobulin antibodies can be used to isolate human immunoglobulins) and antigen affinity chromatography. See, e.g., Coligan et al., supra. Although conventional antibody purification techniques using Protein A and Protein G (e.g., Protein A or Protein G chromatography) could sometimes be utilized to isolate the antibodies of the invention, in many cases this would not be feasible because an object of the invention is to remove antibody binding to such bacterial Fc-binding proteins. For example, to isolate anti-*S. aureus* antibodies that bind Protein G but not Protein A, Protein G chromatography could be used. Rather than using Protein A or Protein G to positively select the antibodies of the invention, Protein A or Protein G can be used to remove Protein A or Protein G reactive antibodies from the antibodies of the invention.

Standard techniques in immunology and protein chemistry can be used to analyze and manipulate the antibodies of the invention. For example, dialysis can be used to alter the medium in which the antibodies are dissolved. The antibodies may also be lyophilized for preservation. Antibodies can be tested for the ability to bind specific antigens using any one of several standard methods such as Western Blot, immunoprecipitation analysis, enzyme-linked immunosorbent assay (ELISA), and radioimmunoassay (RIA). See, e.g., Coligan et al., supra.

Bacteria and Bacterial Antigens

Antigens useful for the production and testing of the antibodies of the invention can be obtained from commercial sources, or isolated from animals or humans harboring the bacteria of interest by conventional techniques in microbiology. For example, dried *S. aureus* (Sigma, St. Louis, Mo., 1997 Catalog, Cat.#S0504); formalin-fixed, non-Protein A-producing *S. aureus* (Sigma, Cat.#S2014); formalin-fixed, Protein A-producing (Cowan strain) *S. aureus* (Sigma, Cat.#P7155); and formalin-fixed Group C streptococci (Sigma, Cat. #P2169) are commercially available. Additionally, a large number of different *S. aureus* isolates (e.g., ATCC Numbers 6341, 9996, and 33497) and Group C streptococcus isolates (e.g., ATCC numbers 12388 and 9342) may be purchased from American Type Culture Collection (Rockville, Md.). Alternatively, infectious bacteria such as *S. aureus* or Group C Streptococci may be obtained from an infected host by isolation and culture (e.g., a site of infection is swabbed, the swab is used to inoculate sterile culture medium suitable for growing the bacterial strain of interest, the culture is incubated under conditions that promote bacterial growth, and bacteria are then isolated from the culture).

Purified antigens derived from bacteria such as *S. aureus* (e.g., enterotoxin A and B, Sigma Cat. #S9399 and S4881) or streptococci (e.g., streptolysin O and S, Sigma Cat.#S5265 and S2888) can be obtained commercially or isolated from whole bacteria by techniques known in the art. For example, proteins contained in a sample of *S. aureus* or Group C streptococci can be separated according to size by SDS-polyacrylamide gel electrophoresis (see, Ausubel et al, supra; Laemmli, U.K., *Nature* 227:680-685, 1970) or by size and isoelectric point using two dimensional gel electrophoresis (O'Farrell, P. H., *J. Biol. Chem.* 250: 4007-4021, 1975). After staining to reveal the location of proteins, specific antigens can be excised from the gel and used to immunize host animals. In another example, purified *S. aureus* capsular polysaccharide antigens can be prepared as described in U.S. Pat. No. 5,770,208 and Fattom et al., *Infect. Immun.* 61:1023-1032 (1993).

Protein A

Protein A is widely available from commercial suppliers. It is available in many forms including the native protein isolated from S. aureus (e.g., Sigma Cat. #P3963), recombinantly-produced (e.g., Sigma Cat. #P7837), and recombinantly-produced with modifications (e.g., IgG binding domain only, Sigma Cat. #P2164). Any form which retains affinity for the constant region of immunoglobulins can be used. Alternatively, it may be isolated from the Cowan strain of *S. aureus* or from the culture medium of a Protein A-secreting bacterial strain by known methods. E.g., Cohen, S., and Sweeney, H. M., *J. Bact.* 140:1028, 1979.

Protein G

Protein G is also widely available from commercial sources. For example, the native protein isolated from a strain of Group C streptococcus (e.g., Sigma Cat. #P9659), recombinantly-produced (e.g., Sigma Cat. #P5170), and recombinantly-produced with modifications (e.g., Protein G', Sigma Cat. #P4689) are all available commercially. Any form of Protein G which retains affinity for the constant region of immunoglobulins can be used. Alternatively, it may be isolated from Group C streptococci by known methods. E.g., Reis et al., *J. Immunol.*, 132:3098, 1984.

Removal of Bacterial Fc-binding Protein Reactivity from Antibodies

Bacterial Fc-binding protein reactivity (e.g., Protein A or Protein G binding) is adsorbed from a solution of antibody by first incubating the bacterial Fc-binding protein with the antibody solution under conditions in which the bacterial Fc-binding protein usually binds antibodies (e.g., room temperature, in phosphate-buffered saline at about pH 7.0-8.0), and then separating the antibodies which are unbound to the bacterial Fc-binding protein from the antibodies which are bound to the bacterial Fc-binding protein. For example, an insoluble form of Protein A (e.g., Protein A-acrylic beads, Sigma Cat. #P1052; Protein A-agarose, Sigma Cat. #P0932; and Protein A-sepharose, Sigma Cat.#P9424) is added to the antibody solution. The solution is then mixed (e.g., tumbled) under conditions which allow antibody binding to Protein A. The insoluble Protein A (along with the Protein A-binding antibodies) is then separated from the supernatant by filtration. The resulting supernatant contains antibodies enriched for non-Protein A binding immunoglobulins. Protein A affinity column chromatography can also be used to isolate non-Protein A binding antibodies from a solution containing both Protein A and non-Protein A binding antibodies. See, e.g., Coligan et al., supra. Here, the antibodies not bound to the Protein A matrix are collected (i.e., those antibodies which elute from a column containing a Protein A matrix using a low salt buffer of about neutral pH). In a like manner, an insoluble form of Protein G can used to enrich a solution of antibodies for immunoglobulins that do not bind protein G. See, id.

Removal of bacterial Fc-binding protein reactivity from a solution of antibodies is not necessary for the invention when the solution of antibodies does not originally contain immunoglobulins that bind bacterial Fc-binding proteins. For example, a cocktail of different human monoclonal antibodies which specifically bind to *S. aureus* but do not have constant regions that specifically bind Protein A can be used (e.g., human monoclonal antibodies of subclass $IgG_3$ having the allotype with arginine at amino acid position 435). Likewise, other monoclonal antibodies that do not bind Protein A can be used (e.g., chicken or goat IgGs).

Conjugation of Antibodies to Antibiotics

The invention includes unmodified antibodies as well as antibodies conjugated with one or more antibiotics. By "antibiotics" is meant any molecule which exhibits a bactericidal or bacteriostatic effect. Included within the term are, for example: classic antibiotics, e.g., chloramphenicol, erythromycin, lincomycin, fusidic acid, streptomycin, other aminoglycoside antibiotics, tetracyclines, polymyxins, fosfomycin, vancomycin, ristocetin, bacitracin, gramacidin, penicillins, and cephalosporins; antimetabolites, e.g., sulfonamides and trimethoprim; and other bactericidal or bacteriostatic agents such as small molecule toxins, radioactive compounds, and nucleoside analogues. Antibiotics can be conjugated to antibodies by methods known in the art (e.g., U.S. Pat. No. 5,545,721, and Means and Feeney, *Chemical Modification of Proteins*, Holden-Day Inc., San Francisco, Calif. 1971). For example, antibiotics can be covalently bonded to an antibody. In another example, antibiotics are non-covalently associated with an antibody (e.g., antibiotic-loaded liposomes are decorated with anti-bacterial antibodies). The method of conjugation should be chosen so that the antibiotic retains its bactericidal or bacteriostatic property when localized to the infection. For example, when it is desired to deliver a high concentration of unconjugated antibiotic to the site of an infection, the antibody-antibiotic bond should be such that it breaks after a short time in the microenvironment of the infection site. Antibodies conjugated with such antibiotics can be administered to an animal or human suffering from a bacterial infection such as a *S. aureus* or streptococcal infection. It is expected that these conjugated antibodies will localize at the site(s) of infection and thereby deliver the antibiotics directly to the bacteria. Moreover, as the antibiotic is targeted to the site of infection via the antibodies, it is likely that higher doses of antibiotics could be used without the degree of side effects that would accompany the use of unconjugated antibiotics. Hence, these antibiotic-conjugated antibodies should be especially useful for delivering a concentrated amount of antibiotic to the site of infection.

Uses

Administration of Pharmaceutical Compositions to Animals or Humans

The pharmaceutical compositions of the invention may be administered to animals or humans in pharmaceutically acceptable carriers (e.g., physiological saline), that are selected on the basis of mode and route of administration and standard pharmaceutical practice. A list of pharmaceutically acceptable carriers, as well as pharmaceutical formulations, can be found in *Remington's Pharmaceutical Sciences*, a standard text in this field, and in USP/NF. Other substances may be added to the compositions to stabilize and/or preserve the compositions. For example, glycine (e.g., 0.3M, pH 6.8), maltose (e.g., 10%) and/or thimerosal (e.g., 1:10,000) may be added to the compositions.

The compositions of the invention may be administered to animals or humans by any conventional technique. Typically, such administration will be parenteral (e.g., intravenous, subcutaneous, intramuscular, or intraperitoneal introduction). The compositions may also be administered directly to the target site (e.g., an abscess) by, for example, surgical delivery to an internal or external target site, or by catheter to a site accessible by a blood vessel. Other methods of delivery, e.g., liposomal delivery or diffusion from a device impregnated with the composition, are known in the art. The composition may be administered in a single bolus, multiple injections, or by continuous infusion (e.g., intravenously or by peritoneal dialysis).

Effective Doses

A therapeutically effective amount is an amount which is capable of producing a medically desirable result in a treated animal or human. As is well known in the medical arts, dosage for any one animal or human depends on many factors, including the subject's size, body surface area, age, the particular composition to be administered, sex, time and route of administration, general health, and other drugs being administered concurrently. It is expected that an appropriate dosage for intravenous administration of antibodies would be in the range of about 0.1 to 100 mg/kg body weight. More specific dosages can be determined by the method described below.

Toxicity and therapeutic efficacy of the compositions of the invention can be determined by standard pharmaceutical procedures, using cells in culture and/or experimental animals to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Antibodies that exhibit large therapeutic indices are preferred. While antibodies that exhibit toxic side effects may be used, care should be taken to design a delivery system that targets such compounds to the site of the infection or tissues to be treated in order to minimize potential damage to uninvolved tissue and thereby reduce side effects.

The data obtained from cell culture assays and animal studies can be used in formulating a range of dosage for use in humans. The dosage of such compounds lies preferably within the range of circulating concentrations that include an ED50 with little or no toxicity. The dosage may vary within this range depending on the dosage form employed and the route of administration utilized.

EXAMPLE

Purification of Non-Protein a Binding Immunoglobulins

*S. aureus* capsular polysaccharide vaccines are prepared as described in Fattom et al., *Infect. Immun.*61:1023-1032 (1993). Human subjects (including those who possess immunoglobulins that have constant regions that do not react with Protein A) are then immunized using the vaccines as described in Fattom et al., id. The subjects are then bled weekly after each immunization and whole cell serum is collected and pooled. The sera are then subjected to Cohn-Oncley cold alcohol fractionation to isolate the immunoglobulins contained within the pooled serum. The isolated immunoglobulins are dissolved in 0.02 M $NaH_2PO_4$ (pH 8.0), 0.15 M NaCl at a concentration of 10 mg/ml. 1.0 ml of Protein A-agarose (Sigma, Cat.#P0932) is added per 1.0 ml of the dissolved immunoglobulins and the mixture is incubated for 2.0 hours at 4 degrees Celsius with gentle tumbling. The mixture is then centrifuged at 20× g for 10 minutes to isolate the supernatant from the Protein A-agarose (and Protein A-bound immunoglobulins). The supernatant which contains the non-Protein A binding immunoglobulins is then removed and filtered using a 0.22 micron filter.

I claim:

1. A composition comprising a polyclonal antibody conjugated with at least one antibiotic, wherein the antibody is purified from pooled human serum and enriched for immunoglobulins comprising an antigen-binding portion that binds a staphylococcal antigen and a constant region that does not bind to staphylococcal Protein A.

2. The composition of claim 1, wherein the antibiotic is selected from the group consisting of chloramphenicol, erythromycin, lincomycin, fusidic acid, streptomycin, an aminoglycoside antibiotic, a tetracycline, a polymyxin, fosfomycin, vancomycin, ristocetin, bacitracin, gramacidin, a penicillin, and a cephalosporin.

3. The composition of claim 1, wherein the antibiotic is an antimetabolite.

4. The composition of claim 3, wherein the antimetabolite is selected from the group consisting of a sulfonamide and trimethoprim.

5. The composition of claim 1, wherein the antibiotic is a small molecule toxin.

6. The composition of claim 1, wherein the antibiotic is a radioactive compound.

7. The composition of claim 1, wherein the antibiotic is a nucleoside analogue.

8. The composition of claim 1, wherein the antibiotic is covalently bonded to the antibody.

9. The composition of claim 1, wherein the antibiotic is non-covalently associated with the antibody.

10. The composition of claim 1, wherein the antibody is conjugated to a liposome loaded with the antibiotic.

* * * * *